(12) United States Patent
Liu

(10) Patent No.: US 6,632,414 B2
(45) Date of Patent: Oct. 14, 2003

(54) MINI-STRUCTURED CATALYST BEDS FOR THREE-PHASE CHEMICAL PROCESSING

(75) Inventor: Wei Liu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/822,159

(22) Filed: Mar. 30, 2001

(65) Prior Publication Data

US 2002/0198419 A1 Dec. 26, 2002

(51) Int. Cl.[7] .............................. C01B 3/26; C07C 5/03; C07C 5/00; C07C 5/10
(52) U.S. Cl. ........................ 423/659; 585/260; 585/262; 585/264; 585/266; 585/270; 585/275; 585/276; 585/277
(58) Field of Search .......................... 423/659; 585/260, 585/262, 264, 270, 266, 275, 276, 277

(56) References Cited

U.S. PATENT DOCUMENTS

| | | | |
|---|---|---|---|
| 3,489,809 A | 1/1970 | Keith et al. | 260/677 |
| 3,885,977 A | 5/1975 | Lachman et al. | 106/62 |
| 4,102,778 A | * 7/1978 | Ruether | 208/143 |
| 4,163,750 A | 8/1979 | Bird et al. | 260/409 |
| 4,529,718 A | 7/1985 | Dupin | 502/439 |
| 4,552,748 A | 11/1985 | Berglin et al. | 423/588 |
| 5,063,043 A | 11/1991 | Bengtsson | 423/588 |
| 5,278,123 A | 1/1994 | Chopin et al. | 502/200 |
| 5,817,901 A | * 10/1998 | Trambouze et al. | 585/259 |
| 6,005,143 A | * 12/1999 | Machado et al. | 564/423 |

FOREIGN PATENT DOCUMENTS

| | | |
|---|---|---|
| EP | 384 905 | 2/1989 |
| EP | 0 319 208 | 6/1989 |
| EP | 319 208 | 6/1989 |
| EP | 667 807 | 11/1994 |
| EP | 885 273 | 12/1996 |
| GB | 963 941 | 7/1964 |
| GB | 1 216 456 | 12/1970 |
| WO | WO 00/42082 | * 7/2000 ............. C08F/8/04 |

OTHER PUBLICATIONS

R. K. Edvinsson et al., "A comparison between the monolithic reactor and the trickle–bed reactor for liquid–phase hydrogenations", *Catalysis Today* 24 (1995), 173–179.

V. Regaini and C. Tine, "Upflow Reactor For The Selective Hydrogenation of Pyrolysis Gasoline—A Comparative Study With Respect to Downflow", *Appl. Catal.*, 10 (1984), 43–51.

A. A. Klinghoffer et al., "Catalytic Wet Oxidation Of Acetic Acid Using Platinum On Alumina Monolith Catalyst", *Catalysis Today*, 40 (1998) 59–7241.

V. Hatziantoniou et al., "Mass Transfer And Selectivity In Liquid–Phase Hydrogenation Of Nitro–Compounds In A Monolithic Catalyst Reactor With Segmented Gas–Liquid Flow", *Ind. Eng. Chem. Process Des. Dev.*, 25 (1986), 964–970.

D.S. Soni and B.L. Crynes, "A Comparison of the Hydrodesulfurization and Hydrodenitrogenation Activities of Monolith Alumina Impregnated with Cobalt and Molybdenum and a Commercial Catalyst", *ACS Symp. Ser.*, 156 (1981), 156–207.

(List continued on next page.)

*Primary Examiner*—Stanley S. Silverman
*Assistant Examiner*—Jonas N. Strickland
(74) *Attorney, Agent, or Firm*—Kees van der Sterre

(57) ABSTRACT

Three-phase chemical hydrogenation reactions involving the processing of gas-liquid reactant feed streams over "mini-structured" solid catalyst beds formed e.g., of channeled honeycomb monoliths incorporating solid catalysts achieve reaction efficiencies suitable for effective integral reactor operation by utilizing low superficial liquid linear velocities and high feedstream gas:liquid ratios; single-pass conversion efficiencies in excess of 50%, typically 80–100%, are achieved.

20 Claims, 1 Drawing Sheet

OTHER PUBLICATIONS

R. K. Edvinsson et al., "Liquid–Phase Hydrogenation of Acetylene in a Monolithic Catalyst Reactor", *Ind. Eng. Chem. Res.*, 34 (94), I11–I114 (1995).

P.G. Menon, M.F.M. Zwinkels, E.M. Johansson, and S.G. Järäs in "Monolithic Honeycombs in Industrial Catalysis", *Kinetics and Catalysis*, 39(5), 615–624 (1998).

A. Cybulski and J.A. Moulijn, "Monoliths in Heterogeneous Catalysis", *Catal. Rev.—Sci. Eng.*, 36(2), 179–270 (1994).

H. A. Smits et al., "Selective Three–Phase Hydrogenation Of Unsaturated Hydrocarbons In A Monolithic Reactor", *Chemical Engineering Science*, 51(11), 3019–3025 (1996).

K. G. Knudsen et al., "Catalytic and Process Technologies for Ultra Low Sulfur Diesel", *Applied Catalysis A: General*, 189 (1999), 205–215.

S. Irandoust and O. Gahne, "Competitive Hydrodesulfurization and Hydrogenation in a Monolithic Reactor", *AIChE Journal*, 36 (5), pp 746–752 (1990).

A. Stankiewicz, "Process intensification in in–line monolithic reactor," *Chemical Engineering Science*, 56 (2001), 359–364.

A. Cybulski et al., "Monolithic Reactors for Fine Chemicals Industries: A Comparative Analysis of a Monolithic Reactor and a Mechanically Agitated Slurry Reactor", *Chemical Engineering Science*, 54 (1999) 2351–2358.

* cited by examiner

MINI-STRUCTURED CATALYST BEDS FOR THREE-PHASE CHEMICAL PROCESSING

BACKGROUND OF THE INVENTION

The present invention relates to the use of structured solid catalyst beds or monolithic catalysts for the efficient processing of gas/liquid feed streams, and more particularly to the processing of such feed streams to carry out hydrotreating and hydrogenation reactions at rapid rates and at high conversion efficiencies.

Fixed bed reactors packed with catalyst pellets in various forms, such as, beads, cylinders, wagon wheels, etc., have been widely used in the chemical processing and refining industries for hydrotreating and hydrogenation processes. Many of these processes are carried out as three-phase (gas-liquid-solid) processes wherein a gas/liquid feed stream is reacted over a solid catalyst. Hydrotreating is an important refinery process for the production of clean (low-sulfur) fuel from petroleum feedstocks, while hydrogenation is widely used for production of a variety of chemicals.

Commercial pellet bed reactors for carrying out such processes, commonly termed "trickle bed" reactors, typically operate in a gas/liquid co-current downflow mode, i.e., a mode wherein both the gas and the liquid reactants flow in the same direction (downwardly) through the catalyst bed. Superficial liquid linear velocities in such reactors, calculated from the length of the catalyst bed and the average transit time for liquid through the bed, are in the range of about 0.01 to 2 cm/s. Trickle bed reactors have been successfully used in the industry for nearly half a century and represent a mature chemical processing technology. Refinements of this technology have involved optimizing catalyst size, shape, and packing method, and by tuning the operating regime, e.g., by employing somewhat higher liquid flow velocities. However, such improvements have been incremental in nature and have not resulted in major enhancements in the efficiencies of these processes.

Over the past two decades, a considerable amount of research effort has been devoted to the development of structured catalysts such as monolith or honeycomb catalysts. Honeycomb monoliths are widely used to support catalysts for the gas-phase processing of combustion engine exhaust gases in automotive catalytic converters. On the other hand, the use of monoliths for carrying out three-phase reactions involving the processing of gas/liquid feedstreams has been quite limited, these reaction systems being very different from gas phase reaction systems.

Of course the low-pressure-drop advantage of honeycomb monolith catalysts is well recognized, and various studies of the behavior of such catalysts have been reported in the literature. However, low pressure drop is only one characteristic affecting catalyst performance in these structures and much attention has focused on trying to understand other reaction performance factors operating in monolithic catalyst beds supporting gas/liquid catalytic reactions. Certainly, from a reactor engineering point of view, three-phase catalytic reaction processes are far more complicated than gas-phase catalytic reactions such as occur, for example, in the monolithic catalysts used in automotive catalytic converters.

In "Catalytic Wet Oxidation Of Acetic Acid Using Platinum On Alumina Monolith Catalyst", *Catalysis Today*, 40 (1998) 59–71, Klinghoffer et al. tested the oxidation of acetic acid over Pt/alumina monolith catalysts in an air/water system. Irandoust and Gahney studied the competitive hydrodesulfurization and hydrogenation of thiophene/cyclohexene over CoMo/alumina monolith catalysts with a simulated mixture in "Competitive Hydrodesulfurization And Hydrogenation In A Monolithic Reactor", *AIChE Journal*, Vol. 36, No.5, 746–752 (1990)).

Hatziantonlou et al. compared the hydrogenation of nitro-compounds over Pd/monolith catalysts to the same hydrogenation in a slurry reactor, but reported a lower reaction rate for the monolith reactor on a catalyst weight-for-weight basis (see "Mass Transfer And Selectivity In Liquid-Phase Hydrogenation Of Nitro-Compounds In A Monolithic Catalyst Reactor With Segmented Gas-Liquid Flow" *Ind. Eng. Chem. Process Des. Dev.*, 25 (1986) 964–970). In "Selective Three-Phase Hydrogenation Of Unsaturated Hydrocarbons In A Monolithic Reactor" *Chemical Engineering Science*, Vol. 51, No. 11, 3019–3025 (1996), Smits et al. tested olefin hydrogenation reactions over Pd/monolith catalysts, and found the reaction rate constants to be highly dependent on liquid linear velocity through the catalyst.

What each of these studies have failed to address is the question of whether such structured catalyst beds have any conversion efficiency advantages over conventional catalyst beds when used in a manner consistent with current commercial catalyst usage. Thus a substantial question remains whether honeycomb monolith or other structured catalyst beds can in fact be useful replacements for the commercial catalyst beds presently used in trickle bed or other conventional gas/liquid reactors. This question of practical utility remains largely unanswered because much of the conversion data reported in the literature has been generated on a laboratory scale in small "differential" reactors, these providing low rates of one-pass conversion, in many cases below 50%. For economic reasons, large commercial reactors are often operated as "integral" reactors, i.e., reactors designed to provide one-pass conversion rates well above 50%, and in many cases near 100%. Unfortunately, it is not possible to extrapolate laboratory findings based on differential reactor data to integral reactor performance, because of the complexity of the reaction coupling and mass transfer interactions involved.

Another uncertainty relates to the fact that previously recorded laboratory results are often predicated on the operation of monolith reactors in the so-called Taylor flow regime. Taylor flow refers to a flow mode characterized by the movement of alternating liquid slugs and gas bubbles of approximately equal size through the channels of a honeycomb catalyst. Maintenance of Taylor flow typically requires reactor operation at relatively high liquid linear velocities (e.g., 30 cm/s) and relatively low gas/liquid ratios (e.g., 0.5 VV). Controlling feed stream flows to meet these requirements may not be feasible in plants designed for carrying out hydrotreating and hydrogenation processes on commercial scales.

Thus it remains to be determined whether structured catalysts such as honeycomb monoliths can provide any advantages over conventional catalyst beds in commercial reactors and, if so, for what reactions and under what reaction conditions can such advantages be secured.

SUMMARY OF THE INVENTION

The present invention provides catalytic conversion processes useful for reactors containing "mini-structured" catalyst beds wherein three-phase chemical reactions such as hydrogenation and hydrotreating can be carried out with high efficiency at conversion rates of practical utility for one-pass or integral reactor systems. By "mini-structured"

catalyst beds is meant catalyst beds that are divided into a number of small catalyzed reaction channels of hydraulic diameter in the order of 0.1 to 10 mm, these being exemplified by honeycomb catalysts of appropriate channel size. In catalyst beds of this structure, the bulk gas and liquid reactant streams are streamlined or divided into separate, small reactant streams that each undergo catalytic reactions inside separate channels.

The reactors used in these processes generally employ solid catalysts and the gas/liquid process feed streams are streams wherein the gas:liquid (G:L) ratio is high. That is, the processes are carried out using relatively high gas flows and relatively low liquid linear velocities to convey the gas/liquid feed streams through the honeycomb catalysts.

More particularly, the invention includes an improved process for carrying out a gas-liquid reaction in the presence of a solid catalyst. In accordance with that process a gas-liquid feed stream comprising gas and liquid reactants is first conveyed through a monolithic structured catalyst bed. The catalyst is provided as a honeycomb or assembly of honeycombs of conventionally channeled structure, i.e., comprising a honeycomb body incorporating a plurality of parallel, open-ended channels running from a first or entrance face to a second or exit face of the body, through which channels the fluids to be treated may freely pass. The channels are formed or bounded by channel walls, these preferably being provided in the form of thin, criss-crossing or intersecting webs of solid material wherein or whereupon the solid catalyst for treating the fluid stream being treated is provided.

In carrying out the process of the invention, the liquid making up the gas-liquid feed stream is conveyed through the honeycomb channels at controlled, limited flow rates. Effective treatment requires that the liquid flow rate be adjusted to insure that the superficial linear velocity of the liquid through the catalyst will be in the range of about 0.01–10 cm/s. The superficial liquid linear velocity of the liquid through the honeycomb catalyst bed is defined in accordance with convention to be the quotient of the length of the catalyst bed divided by the average time required for a small segment of the liquid feed to traverse the bed.

While the liquid is traversing the honeycomb catalyst bed the gas component of the feed stream is conveyed through the bed in a quantity that will maintain a high gas:liquid (G:L) volume ratio in the channels of the honeycomb. Generally, the gas will be provided in a proportion sufficient to maintain a gas:liquid ratio that is in the range of about 1–4000 standard (Normal) liters of gas (NL) for each liter (L) of liquid present, i.e., a G:L ratio from 1:1 to 4000:1 NL/L. For the purpose of the present description a standard or Normal liter of gas is a volume of gas that would occupy one liter at the standard temperature and pressure of 20° C. and 1 atmosphere.

The processing conditions described are useful for carrying out a variety of three-phase reactions over monolithic honeycomb catalyst beds, but are particularly well suited for conducting hydrogenation or hydrotreating reactions using hydrocarbon feedstocks. A variety of unsaturated or substituted hydrocarbon compounds can be efficiently processed by this means. Treatable unsaturated hydrocarbons include the straight- or branched-chain alkenes or alkynes, as well as aromatic hydrocarbons and hydrocarbons incorporating unsaturated hydrocarbon functional groups. Substituted hydrocarbons include those comprising sulfur- or nitrogen-containing functional groups.

It is a particular advantage of the process of the invention that difficult measures to maintain Taylor flow conditions in the honeycomb channels are not required. Instead, one-pass conversion rates in excess of 50% and more typically in excess of 80% of the theoretical conversion limit, are readily obtained for these hydrocarbon reactants regardless of whether Taylor flow is maintained or not, provided the process is conducted within the herein-prescribed ranges of liquid flow and G:L ratio. Thus these processes are suitable for use in single-pass or integrated reactor systems without the need for high recycle rates or supplemental processing equipment.

BRIEF DESCRIPTION OF THE DRAWINGS

The invention may be further understood by reference to the drawings, wherein.

DETAILED DESCRIPTION

The particular reactor design to be selected for carrying out the process of the invention is not critical, but will determined in large part by the chemistry of the particular reaction to be conducted and the environment in which the reaction is to be carried out. In each case, the details of reactor design can readily be selected through the routine exercise of ordinary skill based up the particular reaction to be conducted, the physical plant design, and the feed stream input and product output constraints under which the reactor will be required to operate.

Figure 1:
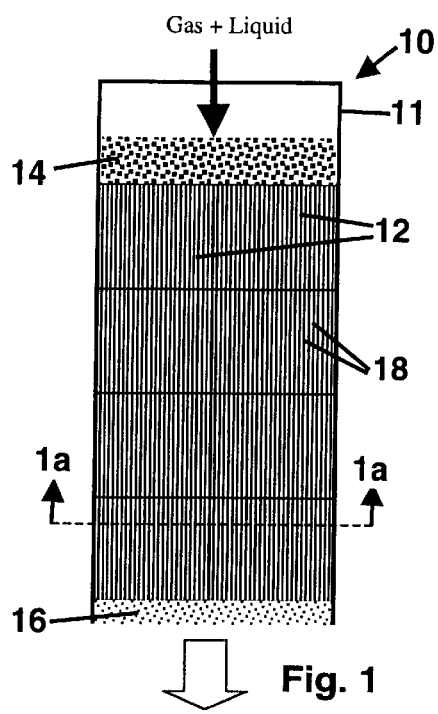
FIGS. 1–1b illustrate a reactor design and catalyst configuration suitable for use in the invention.
Figure 1A:
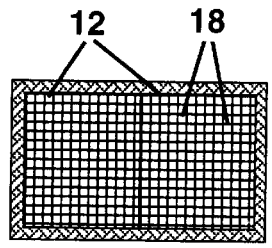
Figure 1B:
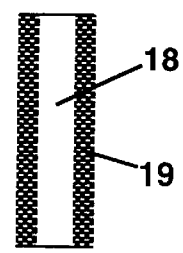

FIGS. 1, 1a, 1b of the drawings schematically present partial views of a reactor utilizing a structured catalyst bed provided as a honeycomb monolith according to the invention, and the components thereof. FIG. 1 presents an elevational cross-section of the reactor (10) incorporating a catalyst packing consisting of an assemblage of honeycomb monolith catalysts 12. These catalysts are better shown in FIG. 1a which is a schematic top plan view of reactor 10 through cross-section 1a—1a in FIG. 1. These structured catalysts can consist of commercially available honeycomb catalyst materials or other catalyst modules having mini-structured configurations in accordance with the invention.

In reactor operation, a gas-liquid feed mixture 14 introduced into reactor enclosure 11 is distributed over the top of monoliths 12 and flows co-currently downwardly through the monolith channels 18 to produce a product mixture 16 at the base of the catalyst stack. FIG. 1b is an enlarged schematic view of one of the channels 18 in structured catalyst 12, that channel being bounded by channel walls 19 comprising a catalyst for processing the feed mixture 14. The selection of the particular catalyst to be employed and the manner in which that catalyst will be arranged within the honeycomb monolith can again be routinely determined depending upon the materials to be processed and the processing conditions to be employed. The critical feature is that the gas and liquid reactant flows be largely confined within separate reaction channels that are catalyzed with solid catalysts. Thus transverse flow between channels is negligible or secondary to the main flow stream along the catalyst channels.

One example of a suitable monolith design includes an extruded honeycomb body composed of a substantially inert porous ceramic material such as cordierite, mullite, alumina or the like, on the interior channel walls of which is coating or dispersion of a suitable catalyst such as a transition metal or a catalytically active metal or combination of metals selected from Groups VIB, VIIB, VIII, and IB of the Periodic Table (CAS version). The selected catalysts may be deposited directly on the channel walls, or they may be carried on or within a porous supporting metal oxide washcoat or other carrier layer applied to the wall surfaces. Alternatively, the catalyst may be carried within the pore structure of the honeycomb, or the honeycomb walls themselves may be formed of an active catalyst. Honeycombs composed of transition metal oxides and other catalytically active materials are well known.

Three different classes of critical parameters determine the efficiency of reactors incorporating structured catalyst beds in accordance with the invention. Most important are (i) the gas and liquid flow conditions, particularly including the liquid linear velocity ($V_l$) and gas/liquid ratio (G/L), that are maintained within the catalyst channels, and (ii) the geometric parameters of the structured catalyst bed, including the hydraulic diameter ($l_c$) of the channel openings, the thicknesses ($l_{cat}$) of the catalyzed walls, the channel density ($n_c$) of the structured catalyst, i.e., the number of channels per unit of catalyst cross-sectional area, the channel shape ($\phi$) and the ratio of channel opening to channel length ($\gamma$). Obviously the activity of the selected catalyst and the reaction conditions employed (temperature, pressure) are a third class of parameters governing reactor efficiency, but these are largely dependent on the specific chemical reactions being conducted. In contrast, the flow conditions and geometric parameters of the catalyst bed have been found to have more generic applicability and importance across a variety of different reaction types.

For most of the liquid hydrocarbon feedstocks amenable to three-phase processing through honeycomb catalysts the honeycomb channels will typically be sized to provide hydraulic diameters in the range of about 0.02–10 mm. Hydrogenation and hydrotreating reactions can be carried out in honeycombs wherein the channel hydraulic diameters are in the narrower size range of 0.1 to 5 mm. Channel openings in these size ranges are comparable in dimensions to the inter-particle void spaces in conventional packed catalyst pellet beds. Catalyst pellet sizes in the pellet beds conventionally used in industry are in the range from about 0.03 to about 0.25 inches. If the channel dimensions are too small, the channels can be plugged by particulates carried in by the feed stream or generated in situ during the treatment process. If the channels are too large, the geometrical surface area of the structured catalyst bed may be too low for efficient gas/liquid/catalyst contacting.

The thickness of the channel walls of commercially available honeycomb catalysts or catalyst supports will normally be in the range of about 0.01 to 5 mm. Wall thicknesses in the range of 0.1 to 2 mm are preferred, both for supporting supplemental catalyst coatings and for the production of honeycombs formed directly of catalytic materials.

The honeycomb cell density (number of channels per unit area of a honeycomb cross-section taken perpendicular to the axis of channel alignment) selected for the honeycomb monoliths to be used for processing may fall anywhere within the range of presently available honeycomb support structures. Cell densities in the range of 10–3000 channels per square inch (cpsi) are useful; cell densities in the range of about 25–400 cpsi are more widely available and quite suitable for most processes.

The ratios of channel length to channel diameter in these structured catalysts will generally be greater than about 10. If this ratio is too small, the performance of the structured catalyst bed begins to approach that of a randomly packed pellet bed in efficiency. Of course, the optimum ratio for any particular reactor environment will be determined by the ease of manufacture and cost of the particular structured catalyst module design employed and constraints that may be imposed by the requirements of reactor assembly, as well as by issues relating to the distribution of gas and liquid flows across the catalyst bed.

Reactors employing honeycomb catalysts for these reactions provide more efficient utilization of the available catalyst surface and volume than trickle bed reactors, as well as enhanced mass transfer of the gas and liquid reactants to the surfaces and into the bulk of the available catalyst. It has generally been perceived that catalyst surfaces in trickle bed hydrogenation reactors are fully or nearly fully wetted. This wetting behavior was thought to insure full utilization of the catalyst under flow conditions of practical interest, e.g., superficial linear liquid flow velocities of 1 cm/s for conventional hydrogenation processes. See, for example, "Liquid-Solid Wetting Factor In Trickle-Bed Reactors: Its Determination By A Physical Method" by Pironti et al. in *Chemical Engineering Science*, 54 (1999) 3793–3800. As hereinafter more fully set forth, however, there are substantial problems with catalyst utilization in the trickle bed reactors conventionally used for hydrogenation and hydrotreating processes, problems which can be substantially overcome utilizing reactors with honeycomb catalysts in accordance with the invention.

Figure 2:
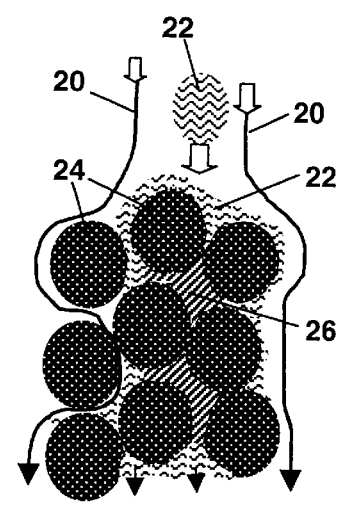
FIG. 2 schematically illustrates a mode of feed stream flow in accordance with prior art.
Figure 3:
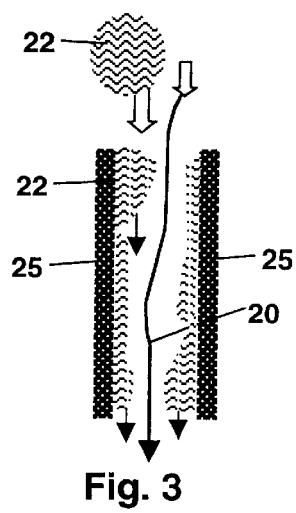
FIG. 3 schematically illustrates a mode of feed stream flow through a structured catalyst in accordance with the invention.

One problem affecting the efficiency of packed pellet bed reactors employing catalyst pellets of typical size (e.g., 1/32" to 1/4" diameter), schematically illustrated in FIG. 2 (prior art) of the drawing, is that of blocked flow. As illustrated in FIG. 2, as hydrogen gas streams (20) and liquid droplets (22) enter a packed catalyst bed and move downwardly through a cluster of catalyst pellets (24), liquid coming into contact with the pellets spreads onto all available catalyst pellet external surfaces. The spreading liquid thus tends to fill voids among the catalyst pellets, and is preferentially trapped by capillary forces in inter-pellet void spaces of appropriate size and shape (26).

Wherever this occurs, the hydrogen gas streams must find other passages through the bed that are not blocked by bound liquid. Thus the portions of the liquid feed stream that become trapped in void spaces in the bed are relatively inaccessible to the reactant gas stream. This effectively reduces catalyst utilization, and at the same time increases the chance of secondary reactions, such as coking, that can occur in stagnant liquid zones due to the relative unavailability of hydrogen. Since it results from the way catalyst pellets are arranged in these reactors, this fundamental disadvantage is inherent in packed bed reactors. That is, even if an ideal uniform flow distribution is created at the entrance to the reactor, there is no way to maintain such uniformity as the gas and liquid flow randomly through the packed bed.

In contrast to packed bed reactors, a key advantage of reactors incorporating honeycomb or other structured catalysts is that bulk gas and liquid flows, even though divided into dimensions similar to the passages between catalyst pellets in a packed bed reactor, are much more resistant to trapping and stagnation. As schematically illustrated in FIG.

3 of the drawing, this results from the fact that liquids (22) coming into contact with the channel walls (25) of the catalyst tend to spread on channel surfaces, leaving free channel space available for gas streams (20) to pass through the catalyst bed. Thus liquid entrapment is unlikely and a more uniform distribution of gases and liquids over the surfaces of the available catalyst is realized. At the same time, surface reactions and the tensile forces applied by the gas flow on the liquid film on the wall further facilitate liquid exchange, i.e., mass transfer from the bulk of the liquid onto the catalyst surface.

The relative performance characteristics of packed bed and honeycomb catalysts can be further analyzed in light of the reaction rate equations applicable thereto. Thus, for hydrogenation or hydrotreating reactions of the general form:

$$\text{Hydrocarbon (liquid)} + \text{Hydrogen (gas)} \rightarrow \text{Product} \qquad (1)$$
$$\phantom{xxxxxxxxxx}A\phantom{xxxxxxxxxxxx}B$$

one can write:

$$R_{app} = f_{L/S} \cdot A_{geo} \cdot \theta_{cat}(\phi_{Th}) \cdot f_{cat} \cdot \alpha \cdot k_{app,S} \cdot C_{A,S} \qquad (2)$$

$$\phi_{Th} = l_{cat} \cdot \sqrt{\frac{k_{app,S}}{D_{eff}}} \qquad (3)$$

$$k_{app,S} = k_s \cdot C_{B,avg} \qquad (4)$$

wherein $R_{app}$ is the apparent reaction rate in mol/(s·m³); $f_{L/S}$ is the fraction of the catalyst outer surface covered by the liquid reactant; $f_{cat}$ is catalyst volume fraction; $A_{geo}$ is the geometrical surface area of the catalyst in m²/m³; $\theta_{cat}$ is the effectiveness factor of the catalyst layer; $\phi_{Th}$ is the Thiele modulus of the reaction in the catalyst; $k_S$ is the intrinsic reaction rate constant; $C_{A,S}$ is the concentration of reactant A at the catalyst outer surface in mol/m³; $C_{B,avg}$ is the kinetically averaged concentration of reactant B inside the catalyst in mol/m³; $l_{cat}$ is the thickness of the catalyst layer on the honeycomb channel in m; $k_{app,s}$ is apparent rate constant per second on the catalyst surface, $D_{eff}$ is the effective diffusivity of reactant A in m²/s in the catalyst; and α is a unit conversion factor.

While the catalyst effectiveness factor $\theta_{cat}$ would be expected to increase with decreasing catalyst thickness, in a honeycomb catalyst the catalyst volume fraction $f_{cat}$ will decrease with decreasing wall thickness, so that no advantage in reaction activity on a reactor volume basis would be expected from thinning the catalyst. Of course, the geometrical surface area of the catalyst bed will increase with decreasing catalyst particle size or channel opening size, and it is known that small catalyst sizes are generally desirable if practically feasible. However, in the trickle bed reactor, use of small size of the catalyst is limited by hydrodynamics, and in honeycomb catalysts reducing the channel size increases the manufacturing cost and increases possibility of channel plugging.

Notwithstanding these factors, the use of honeycomb beds in hydrogenation reactions yields surprisingly high reaction rates even where the geometrical surface area and physical volume of the catalyst are not increased over those of packed pellet beds. Without intending to be bound by theory, the higher rates are presently attributed to (i) higher catalyst surface coverage by hydrocarbon liquid reactant A at any given moment and (ii) higher concentrations of both of reactants A and B on the catalyst surface at any given moment.

As to the advantage of liquid coverage, it can be seen from equation (2) above that the apparent reaction rate $R_{app}$ is directly proportional to the liquid/catalyst contacting efficiency. And, while the liquid/catalyst contact process is clearly both dynamic and complex, it is thought that the simple geometry of the catalyst channel makes it more readily accessible than the packed catalyst pellets by the liquid fluid.

The reactant concentration advantage is thought to arise from the fact that the gas and liquid in the honeycomb catalyst are confined together within a relatively small reaction domain. Equation 4 above indicates that the reaction rate will be zero if either one of the two reactants is not available. In a honeycomb packing, the liquid hydrocarbon film on the channel walls of the honeycomb is continually replenished since capillary liquid trapping in pellet interstices does not occur. Further, the use of an appropriate level of hydrogen flow through the channels will facilitate the breakdown of the liquid hydrocarbon film so that concentrations of both liquid and gas reactants on the catalyst surface are maximized.

Two classes of hydrogenation reactions, i.e., olefin hydrogenation and toluene saturation, are representative of the types of reactions that can benefit from the practice of the present invention. Specific examples of these reactions are as follows:

$$\text{Styrene} + \text{H}_2 \rightarrow \text{Ethylbenzene} \qquad (5)$$

$$\text{1-Octene} + \text{H}_2 \rightarrow \text{N-Octane} \qquad (6)$$

$$\text{Toluene} + 3\text{H}_2 \rightarrow \text{methyl-cyclohexane} \qquad (7)$$

Olefin hydrogenation is a kinetically fast reaction and reaction efficiency depends largely on the nature of the contact between the unsaturated hydrocarbon liquid and the catalyst external surface. These reactions are representative of other hydrogenation reactions involving the saturation of unsaturated chemical bonds in non-aromatic molecular structures. Toluene saturation, on the other hand, is kinetically much slower than the olefin saturation, being representative of the hydrogenation of unsaturated chemical bonds in the aromatic molecular structure. In addition, more hydrogen molecules are required for the aromatic saturation than for the olefin saturation. Similar reactions include the saturation of mono-aromatic and poly-aromatic compounds, or aromatic sulfur compounds including thiophenes, benzothiophenes, and dibenzothiophenes.

The following illustrative examples show some of the advantages of invention for hydrogenation and hydrotreating reactions of the types hereinabove described.

EXAMPLE I (PRIOR ART)

Olefin Hydrogenation—Packed Bed (Trickle) Reactor 10 cc of ⅛" Ni/alumina catalyst beads are loaded along with an SiC powder diluent into a tube reactor of 1 inch diameter. The SiC diluent consists of 40 cc of 60 mesh SiC powder. Additional quantities of SiC powder being used to form supporting end plugs for the catalyst within the reactor.

The catalyst thus loaded is then pre-reduced by flowing hydrogen through the reactor at a reactor pressure of 220 psig and a reactor temperature of 400° C. for 10 hours followed by cooling. After the hydrogen pre-treatment a liquid reactant consisting of 5% 1-octene, 5% styrene, and 90% toluene is combined with a stream of flowing hydrogen gas in a reactor delivery tube, the combined stream is pre-heated to a predetermined reaction temperature, and the heated stream is then introduced into the top of the reactor as a gas/liquid feed stream.

The feed stream thus introduced into the reactor is caused to flow downwardly through the reactor in a co-current flow mode, passing through the catalyst bed where the styrene and 1-octene are hydrogenated to yield a product stream comprising ethylbenzene and n-octane, respectively. This product stream is then cooled and separated into gas and liquid products, with the liquid product being analyzed to determine the conversion efficiency of the reactor.

The olefin conversions for each of 1-octene and styrene provided by this reactor under various reaction conditions are reported in Table 1 below. Included in Table 1 for each set of reaction conditions reported are the reactor pressure maintained during the run, in psig, the H2/oil ratio (liters of hydrogen gas at standard temperature and pressure [NL] to liters of hydrocarbon liquid [L]), the liquid-hourly-space-velocity (LHSV) of the mixed feed stream through the reactor, the reactor temperature measured at the bottom of the catalyst bed, the percent conversions of the styrene and 1-octene to their respective hydrogenated products, and the calculated 1-octene conversion activity of the catalyst calculated from the 1-octene hydrogenation conversion percentage and the liquid-volume space velocity.

EXAMPLE II

Olefin Hydrogenation—Ideal Packed Bed

Ni/alumina catalyst beads of the same composition and form as used above in Example I are packed individually into a ¼-inch diameter stainless steel reactor tube approximately 12" long. The inner diameter of the tube (about 3 mm) is only slightly larger than the pellet diameter, providing a column of single pellets with clearance for feed stream flow within the tube. The catalyst packing volume and void fraction for this arrangement are about 2.15 cc and 0.33, respectively.

The catalyst pellets are pre-reduced in situ with flowing hydrogen gas supplied at 220 psig and a temperature of 400° C. for 10 hours. A mixed gas/liquid feed stream consisting of hydrogen gas and a blend of liquid hydrocarbon reactants is then introduced through a delivery tube into top of the reactor and flowed downwardly over the catalyst. The reactant blend is made up of 0.5 wt. % 1-octene, 0.5 wt. % styrene, and 99 wt. % toluene. The hydrogen and liquid are mixed in the delivery tube and preheated to a suitable reaction temperature prior to contact with the catalyst.

TABLE 1

Olefin Hydrogenation - Packed Bed Reactor

| Reactor pressure (psig) | H$_2$/Oil (NL/L) | LHSV (1/h) | Bed bottom Temp. (° C.) | Styrene conversion (wt. %) | 1-octene conversion (wt. %) | 1-octene Conversion Activity (V/V/S) |
|---|---|---|---|---|---|---|
| 220 | 50 | 12 | 74.2 | 90.6 | 72.0 | 0.0042 |
| 220 | 50 | 24 | 73.0 | 68.5 | 38.7 | 0.0033 |
| 220 | 50 | 48 | 60.6 | 43.0 | 16.8 | 0.0025 |
| 220 | 50 | 6 | 29.1 | 71.1 | 52.5 | 0.0012 |
| 220 | 50 | 12 | 31.3 | 50.3 | 29.4 | 0.0012 |
| 220 | 50 | 24 | 31.0 | 38.0 | 17.2 | 0.0013 |
| 220 | 50 | 48 | 30.9 | 30.3 | 9.0 | 0.0013 |
| 50 | 50 | 12 | 69.3 | 72.1 | 48.3 | 0.0022 |
| 110 | 50 | 12 | 67.4 | 77.5 | 62.3 | 0.0033 |
| 220 | 50 | 12 | 68.7 | 89.0 | 74.7 | 0.0046 |
| 220 | _12_ | 12 | 66.2 | 82.9 | 52.3 | 0.0025 |
| 220 | _25_ | 12 | 68.7 | 89.0 | 74.7 | 0.0046 |
| 220 | _50_ | 12 | 70.6 | 90.2 | 81.4 | 0.0056 |

The calculated 1-octene conversion efficiencies reported in Table I provide a convenient basis for comparing the hydrogenation performance of different catalyst loadings and catalyst configurations in reactors of common design. As the data in Table I suggest, conversion efficiency in this packed bed reactor design appears to increase somewhat with LHSV and decrease somewhat with decreasing temperature, if reactor pressure and feed H2/oil volume ratio are maintained the same. Also, under constant LHSV and nearly constant temperature conditions, conversion efficiency increases with pressure and feed H2/oil ratio.

Further information relating to the efficiency of pelletized hydrogenation catalysts for gas/liquid hydrogenation processing is provided by data from the testing of a reactor wherein the packing of the catalyst pellets is idealized to reduce flow channeling and other effects limiting reactor efficiency, in accordance with the following procedure.

Gas/liquid flows in this ideally packed reactor are restricted to a scale of about the catalyst bead size, and are relatively regular compared to the random and tortuous flow paths followed by reactants in a conventional trickle bed reactor.

The olefin conversions observed under various conditions in this reactor are reported below in Table 2. Included in Table 2 for each of the runs conducted are the temperatures measured at the top and bottom of the catalyst bed, in ° C., the calculated average linear velocity of liquid reactant flow through the reactor, in cm/sec, the H2/oil ratio (liters of hydrogen gas at standard temperature and pressure [NL] to liters of hydrocarbon liquid [L]), the liquid-hourly-space-velocity (LHSV) of the mixed feed stream through the reactor, the percent conversions of the styrene and 1-octene to their respective hydrogenated ethyl benzene (EB) and n-octane products, and the measured 1-octene conversion activity of the catalyst calculated from the 1-octene conversion percentage and liquid-hourly-space-velocity (LHSV) through the reactor. All reactions are carried out at a reactor pressure of 220 psig.

TABLE 2

Olefin Hydrogenation - Ideal Packed Bed

| Bed temp. (° C.) | | $V_L$ | LHSV | $H_2$/Oil | Styrene to | 1-octene to | 1-octene Conversion |
|---|---|---|---|---|---|---|---|
| Top | Bottom | (cm/s) | (1/h) | (NL/L) | EB (%) | n-octane (%) | Activity (V/V/sec) |
| 63.7 | 67.2 | 0.12 | 13.9 | 20 | 55.4 | 48.7 | 0.0026 |
| 63.5 | 66.6 | 0.12 | 13.9 | 100 | 89.0 | 80.8 | 0.0064 |
| 61.5 | 64.5 | 0.47 | 55.7 | 5 | 42.4 | 35.8 | 0.0069 |
| 60.6 | 64.1 | 0.47 | 55.7 | 50 | 49.8 | 44.4 | 0.0091 |
| 61.1 | 66.1 | 0.83 | 97.5 | 20 | 40.7 | 34.6 | 0.0115 |
| 53 | 78.6 | 2.36 | 278.6 | 5 | 75.5 | 61.1 | 0.0731 |

As the data in Table 2 suggest, conversion and activity results for the ideally packed reactor design of Example II are generally more favorable than the results for the conventional trickle bed reactor design of Example I, if compared under similar reaction conditions and at similar flow rates. These results suggest that ineffective gas/liquid/catalyst surface contacting is a substantial factor limiting the efficiency of conventional trickle bed reactors.

As the data in Table II also suggest, hydrogenation activity of the ideally packed catalyst depends directly on the liquid velocity and hydrogen flow rate relative to the liquid flow rate through the reactor. For example, when the liquid feed rate is increased to raise the liquid velocity through the reactor by a factor of 7, i.e., from 0.12 cm/s to 0.83 cm/s, the 1-octene conversion slightly decreases but the apparent 1-octene conversion activity of the catalyst increases by approximately a factor of 4, i.e., from 0.0026 to 0.115 v/v/s.

Still further reactor performance advantages for hydrogenation and hydrotreating reactions are secured through the use of honeycomb packings to replace packed pellet beds, as shown in the following illustrative examples.

EXAMPLE III

Olefin Hydrogenation—Structured Catalyst with Catalyst-Coated Wall

A structured monolithic catalyst of square-channeled honeycomb configuration, having a diameter of 1 cm and a length of 30 cm in the direction of channel orientation in the honeycomb, is prepared by impregnating an alumina-washcoated cordierite honeycomb substrate with a Ni nitrate solution. The washcoated monolith has a nominal channel diameter of 1 mm, a channel wall thickness of about 0.2 mm, and a channel density of 400 cpsi measured in a plane transverse to the direction of channel orientation in the honeycomb. The thickness of the Ni/alumina catalyst layer after nickel impregnation of the washcoat is about 0.05 mm.

To separate catalyst performance from feed stream distribution effects, a single channel on the catalyst module is isolated for testing purpose by plugging other channel openings on the top and bottom of the honeycomb with liquid-impervious cement. A stainless steel delivery tube of ⅛" O.D. is then mounted with the cement on the top of the isolated channel.

The catalyst module thus prepared is positioned within a tube reactor of 2 cm diameter surrounded by a bedding of SiC powder. The catalyst monolith is then pre-reduced in situ by flowing hydrogen through the reactor at 220 psig at 400° C. for 10 hours.

After the catalyst has been thus prepared, a gas/liquid feed stream consisting of hydrogen gas and a blended hydrocarbon liquid reactant is delivered into the catalyst channel through the stainless steel delivery tube and flowed downwardly through the catalyst monolith. The gas and liquid mixture is preheated to a predetermined reaction temperature prior to contact with the catalyst. Following treatment over the catalyst, the reactor effluent is cooled below room temperature and separated into off gas and liquid product. The liquid product is then analyzed to determine the extent of the hydrogenation of each of styrene to ethylbenzene and 1-octene to n-octane.

Several conversion runs utilizing a range of different reaction conditions are evaluated using this reactor, and two different liquid feed streams are used for these runs. Feed I consists of 5 wt. % 1-octene, 5 wt. % styrene, and 90 wt. % toluene, while Feed II consists of 0.5 wt. % styrene, 0.5 wt. % 1-octene, and 99 wt. % toluene. By increasing the feed stream flow rate into the reactor, conversion data over a range of liquid linear velocities and liquid hourly space velocities can be generated.

Typical results of this testing are reported in Table 3 below. Included in Table 3 for each of the runs conducted are: the temperatures measured at the top and bottom of the catalyst bed, in ° C., the calculated average linear velocity of liquid reactant flow through the reactor, in cm/sec, the reactor pressure at which the run is carried out, in psig, the H2/oil ratio (liters of hydrogen gas at standard temperature and pressure [NL] to liters of hydrocarbon liquid [L]), the liquid-hourly-space-velocity (LHSV) of the mixed feed stream through the reactor, the percent conversions of the styrene and 1-octene to their respective hydrogenated ethyl benzene (EB) and n-octane products, and the measured 1-octene conversion activity of the catalyst as calculated from the conversion percentage and liquid-hourly-space-velocity (LHSV) of the feed stream through the reactor.

TABLE 3

Olefin Hydrogenation - Structured Catalyst

| Bed temp. (° C.) | | $V_L$ | Pressure | LHSV | $H_2$/Oil | Styrene to EB | 1-octene to | 1-octene Conversion |
|---|---|---|---|---|---|---|---|---|
| Top | Bottom | (cm/s) | (psig) | (1/h) | (NL/L) | (%) | n-octane (%) | Activity(V/V/sec) |
| Feed I [10 wt. % olefins] | | | | | | | | |
| 63.6 | 63.3 | 0.83 | 220 | 107 | 20 | 92.8 | 76.9 | 0.082 |
| 60.9 | 73.2 | 6.67 | 220 | 859 | 20 | 79.9 | 52.4 | 0.395 |
| 62.5 | 60.6 | 0.83 | 220 | 107 | 100 | 99.7 | 88.8 | 0.092 |
| 60.8 | 68.8 | 3.33 | 220 | 429 | 50 | 84.9 | 66.6 | 0.278 |
| 59.3 | 71.9 | 6.67 | 220 | 859 | 50 | 74.9 | 50.1 | 0.393 |
| 60.9 | 76.6 | 16.67 | 220 | 2147 | 50 | 58.3 | 29.2 | 0.557 |
| 61.1 | 72.3 | 6.67 | 110 | 859 | 50 | 68.2 | 37.6 | 0.279 |
| 59.3 | 71.9 | 6.67 | 220 | 859 | 50 | 75.0 | 50.1 | 0.393 |
| 61.2 | 72.7 | 6.67 | 350 | 859 | 50 | 70.6 | 53.2 | 0.435 |
| Feed II [1 wt. % olefins] | | | | | | | | |
| 61.8 | 62.9 | 0.83 | 220 | 107 | 20 | 99.7 | 94.4 | 0.088 |
| 61.3 | 64 | 6.67 | 220 | 859 | 50 | 97.1 | 84.8 | 0.480 |
| 60.8 | 63.5 | 16.67 | 220 | 2147 | 50 | 81.6 | 65.9 | 0.721 |

The hydrogenation conversion rates and catalytic activities observed in the course of this testing are unexpectedly high. For example, at a liquid linear flow velocity of 0.83 cm/s, styrene conversion rates in excess of 99% are obtained with either feed stream notwithstanding the relatively short (30) cm length of the reactor. Further, although the extent of conversion decreases with increasing LHSV through the reactor, significant one-pass conversions for these hydrogenations are obtained for all the testing conditions listed in Table 3. Thus for many chemical processes carried out on a commercial scale, monolithic catalysts enable integrated or one-pass hydrogenation reactor operation, as opposed to differential reactor operation that would incur large recycling costs.

The difference in the underlying hydrogenation activities of the structured and pelletized catalysts tested as above described is even more surprising. The tabular data in Tables 1–3 suggest that the structured catalysts of Example III demonstrate 1-octene hydrogenation activities that are from one to two orders of magnitude higher than the corresponding activities calculated for the pellet bed catalysts of Examples I and II. For example, at a linear liquid velocity level of about 0.83 cm/sec using a feed $H_2$/oil ratio of 20 NL/L and a feed temperature of about 61° C., the olefin hydrogenation activity of the ideal packed bed reactor at an operation pressure of 220 psig is about 0.0115 sec-1. Under similar conditions the structured catalyst reactor operates at an apparent hydrogenation activity level of 0.088 sec-1. This approximately 7.6-fold increase in catalyst activity for the structured catalyst could not be predicted from its small geometric surface area advantage over the pelletized catalyst (2300 $m^2/m^3$ for the monolith versus 1400 $m^2/m^3$ for the pellet bed). These data support the conclusion that the active catalyst surfaces of the pellets in the packed bed reactors are underutilized

EXAMPLE IV

Olefin Hydrogenation—Structured Catalyst with Bulk Catalyst Wall

Structured catalyst support monoliths of cylindrical honeycomb configuration, having a diameter of 1 cm. and a length of 30 cm in the direction of the honeycomb channels, are prepared for testing. Two monolith configurations are selected, both being composed substantially entirely of porous gamma alumina. The first configuration incorporates square channels of 1 mm in diameter bounded by channel walls of 0.18 mm thickness at a channel density of 400 cpsi. The second configuration incorporates square channels of the same diameter, but the channel walls are 0.71 mm in thickness and the channel density is 200 cpsi.

The porous walls of these honeycomb supports are filled with an active hydrogenation catalyst by immersing the honeycombs in an aqueous 2 M nickel nitrate solution, removing the honeycomb from the solution and clearing the honeycomb channels with compressed air, drying the impregnated honeycomb in an oven at 100° C. for about 16 hours, and finally calcining the dried honeycomb in air in a furnace at 400° C. for 2 hours to convert the nickel salt therein to nickel oxide. The fully catalyzed 400 cpsi honeycomb thus provided has a NiO loading of about 9.3 wt. % distributed throughout the wall structure of the honeycomb, with the porous walls having a BET surface area of 214 $m^2/g$. The 200 cpsi honeycomb has a catalyst loading of 9.0 wt. % and the walls have a BET surface area of 190 $m^2/g$.

These Ni/alumina catalysts are tested for dehydrogenation activity utilizing the procedure set forth above in Example III. The liquid feed used to evaluate the catalysts consists of 0.5 wt. % styrene, 0.5 wt. % 1-octene, and 99 wt. % toluene. The results of testing are set forth in Table 4 below. Included in Table 4 for each of the hydrogenation runs conducted are: the temperatures measured at the top and bottom of the catalyst bed, in ° C., the calculated average linear velocity $V_L$ of liquid reactant flow through the reactor, in cm/sec, the reactor pressure at which the run is carried out, in psig, the H2/oil ratio (liters of hydrogen gas at standard temperature and pressure [NL] to liters of hydrocarbon liquid [L]), the percent conversions of the styrene and 1-octene to their respective hydrogenated ethyl benzene (EB) and n-octane products, and the measured 1-octene conversion activity of the catalyst as calculated from the conversion percentage and liquid-hourly-space-velocity (LHSV) of the feed stream through the reactor.

TABLE 4

Olefin Hydrogenation - Bulk Structured Catalysts

| Bed temp. (° C.) | | $V_L$ | Pressure | $H_2$/Oil | Styrene to EB | 1-octene to | 1-octene Conversion |
|---|---|---|---|---|---|---|---|
| Top | Bottom | (cm/s) | (psig) | (NL/L) | (%) | n-octane (%) | Activity(V/V/sec) |
| 400 cpsi catalyst | | | | | | | |
| 61 | 74.5 | 0.83 | 220 | 100 | 99.5 | 92.9 | 0.073 |
| 61.2 | 65.9 | 1.67 | 220 | 50 | 95.9 | 89.4 | 0.125 |
| 61.4 | 66.2 | 3.33 | 220 | 50 | 96.3 | 89.9 | 0.254 |
| 60.9 | 70.8 | 6.67 | 220 | 50 | 91.0 | 80.2 | 0.360 |
| 58.4 | 73.2 | 16.67 | 220 | 50 | 74.9 | 58.3 | 0.486 |
| 200 cpsi catalyst | | | | | | | |
| 60.1 | 60.7 | 0.94 | 220 | 44.4 | 97.7 | 92.6 | 0.082 |
| 58.9 | 62.4 | 1.61 | 220 | 51.8 | 96.4 | 91.1 | 0.130 |
| 61.8 | 68.9 | 6.47 | 220 | 51.5 | 83.1 | 77.3 | 0.320 |
| 62.7 | 70.6 | 15.1 | 220 | 55.3 | 79.6 | 62.7 | 0.496 |

As is evident from a study of the data in Table 4, 60% or higher one-pass olefin conversions are obtained over the entire liquid linear velocity range from 0.83 to 15.0 cm/s. with these structured catalysts. The data also suggests that increasing the bulk of catalyst present in the wall structure of the monoliths offers little advantage in terms of catalyst activity or conversion efficiency. Therefore, again, the contacting efficiency between the liquid reactant and the catalyst surface appears to be the principal factor affecting hydrogenation performance in these reactors.

EXAMPLE V

Olefin Hydrogenation—Structured Catalyst with Bulk Catalyst Wall

A structured catalyst is prepared by impregnating a square-channeled cylindrical gamma alumina honeycomb monolith substrate with a Ni nitrate solution as in Example IV. The substrate selected has a diameter of 1 cm and a cylinder length of 30 cm, with a channel density of 100 cpsi, a channel wall thickness of 0.64 mm, and a channel diameter of 2 mm. Following catalyst impregnation the catalyzed monolith has a catalyst loading of 9.0 wt. % NiO and a BET surface area of 187 $m^2$/g. This catalyst configuration is of because its geometric surface area (GSA) is very similar to that of the idealized packed pellet bed catalyst evaluated in Example II above.

When tested for hydrogenation activity using a liquid feed containing 0.5 wt. % styrene, 0.5 wt. % 1-octene, and 99 wt. % toluene in accordance with the procedure described in Example II. the performance data set forth in Table 5 below are generated. Included in Table 5 for each of the hydrogenation runs conducted are: the temperatures measured at the top and bottom of the catalyst bed, in ° C., the calculated average linear velocity $V_L$ of liquid reactant flow through the reactor, in cm/sec, the reactor pressure at which the run is carried out, in psig, the H2/oil ratio (liters of hydrogen gas at standard temperature and pressure [NL] to liters of hydrocarbon liquid [L]), the percent conversions of the styrene and 1-octene to their respective hydrogenated ethyl benzene (EB) and n-octane products, and the measured 1-octene conversion activity of the catalyst as calculated from the conversion percentage and liquid-hourly-space-velocity (LHSV) of the feed stream through the reactor.

TABLE 5

Olefin Hydrogenation - Reduced GSA Structured Catalyst

| Bed temp. (° C.) | | $V_L$ | Pressure | $H_2$/Oil | Styrene to EB | 1-octene to | 1-octene Conversion |
|---|---|---|---|---|---|---|---|
| Top | Bottom | (cm/s) | (psig) | (NL/L) | (%) | n-octane (%) | Activity(V/V/sec) |
| 63.2 | 67.6 | 0.21 | 220 | 100 | 99.6 | 93.9 | 0.020 |
| 60.4 | 67.4 | 0.42 | 220 | 50 | 100.0 | 94.5 | 0.041 |
| 60.7 | 66.8 | 0.83 | 220 | 50 | 81.6 | 58.1 | 0.024 |
| 60.6 | 71.1 | 1.67 | 220 | 50 | 64.3 | 42.9 | 0.031 |
| 60.3 | 76.6 | 4.17 | 220 | 50 | 62.4 | 35.3 | 0.061 |
| 60.5 | 66.7 | 0.83 | 220 | 7.5 | 87.7 | 75.6 | 0.039 |
| 60.8 | 67.1 | 0.83 | 220 | 25 | 81.1 | 67.2 | 0.031 |
| 60.7 | 66.8 | 0.83 | 220 | 50 | 81.6 | 58.1 | 0.024 |
| 60.8 | 67 | 0.83 | 220 | 100 | 80.9 | 56.2 | 0.023 |
| 60.7 | 72.2 | 4.17 | 220 | 2.5 | 28.1 | 16.5 | 0.025 |
| 60.3 | 74.2 | 4.17 | 220 | 5 | 50.6 | 28.7 | 0.047 |
| 60.2 | 74.7 | 4.17 | 220 | 10 | 56.6 | 32.6 | 0.055 |
| 60.2 | 75.6 | 4.17 | 220 | 25 | 61.7 | 35.1 | 0.060 |
| 60.3 | 76.6 | 4.17 | 220 | 50 | 62.4 | 35.3 | 0.061 |

The data in Table 5 show that one-pass conversions above 90% for both styrene and 1-octene can be achieved in this catalyst at superficial liquid linear velocities as low as 0.21 cm/s. Other observed effects include a slight decrease in olefin conversion with increasing feed $H_2$/oil ratio at a liquid stream velocity $V_L$ of 0.83 cm/s, but an increase in olefin conversions at higher $H_2$/oil ratios at 4.17 cm/s.

The performance of this structured catalyst also offers a clear advantage over the performance of the idealized packed pellet bed of Example II, when compared at similar liquid flow velocities (0.42 cm/s and 0.47 cm/s, respectively) and similar H2/oil ratios (50 NL/L). these flow rates are not dissimilar to the flows employed in commercial pellet bed reactors, yet the hydrogenation activity of the structured catalyst of this Example V (0.041 l/s) is more than four times the 0.0091 l/s activity level seen in the packed pellet bed reactor. Again this activity advantage can be attributed to the more efficient gas/liquid catalyst contact maintained in the structured catalyst reactor.

The results of these tests are reported in Table 6 below. Included in Table 6 for each of the hydrogenation runs conducted are: the temperatures measured at the top and bottom of the catalyst bed, in ° C., the calculated average linear velocity $V_L$ of liquid reactant flow through the reactor, in cm/sec, the reactor pressure at which the run is carried out, in psig, the H2/oil ratio (liters of hydrogen gas at standard temperature and pressure [NL] to liters of hydrocarbon liquid [L]), the feed toluene concentration as a weight percentage of the toluene-methylcyclohexane feed, the percent conversion of toluene to methylcyclohexane in a single pass through the reactor, and the apparent toluene conversion activity of the catalyst as calculated from the percent toluene conversion and liquid-hourly-space-velocity (LHSV) of the feed through the reactor, based on the assumption of first order reaction kinetics.

TABLE 6

Toluene Saturation - Structured Catalyst

| Bed temp. (° C.) | | $V_L$ | Pressure | $H_2$/Oil | Feed Toluene | Toluene | Toluene Conversion |
|---|---|---|---|---|---|---|---|
| Top | Bottom | (cm/s) | (psig) | (NL/L) | Concentration (%) | conversion (%) | Activity (V/V/sec) |
| 148 | 170 | 1.59 | 220 | 50 | 1.2 | 83.5 | 0.094 |
| 151 | 171 | 1.59 | 220 | 50 | 2.6 | 82.9 | 0.093 |
| 152 | 170 | 1.59 | 220 | 50 | 4.2 | 73.5 | 0.069 |
| 152 | 161 | 0.27 | 220 | 50 | 4.3 | 99.3 | 0.043 |
| 151 | 157 | 0.80 | 220 | 50 | 4.3 | 93.7 | 0.076 |
| 152 | NA | 1.59 | 220 | 50 | 4.3 | 73.5 | 0.069 |
| 148 | NA | 3.98 | 220 | 50 | 4.3 | 27.1 | 0.041 |
| 150 | NA | 0.80 | 220 | 25 | 4.3 | 88.1 | 0.056 |
| 151 | 157 | 0.80 | 220 | 50 | 4.3 | 93.7 | 0.076 |
| 151 | NA | 0.80 | 220 | 100 | 4.3 | 84.9 | 0.049 |
| 101 | 112 | 0.80 | 220 | 50 | 4.2 | 85.2 | 0.050 |
| 134 | 131 | 0.80 | 220 | 50 | 4.2 | 95.7 | 0.082 |
| 151 | 157 | 0.80 | 220 | 50 | 4.2 | 93.7 | 0.076 |
| 185 | 186 | 0.80 | 220 | 50 | 4.2 | 77.3 | 0.039 |
| 100 | 113 | 1.59 | 110 | 50 | 2.6 | 46.7 | 0.033 |
| 108 | 109 | 1.59 | 220 | 50 | 2.6 | 64.6 | 0.055 |
| 100 | 111 | 1.59 | 440 | 50 | 2.6 | 60.5 | 0.048 |

EXAMPLE VI

Aromatic Saturation—Structured Catalyst with Bulk Catalyst Wall

A gamma alumina honeycomb substrate having the same configuration as the substrate of Example V, except for an increase in the channel wall thickness to 1.0 mm and a change in channel shape to a circular channel cross-section, is impregnated with a nickel oxide catalyst in accordance with the procedure of Example III. The catalyst monolith thus provided has a catalyst loading of 7.35 wt. % NiO and a BET surface area of 175 $m^2$/g.

This catalyst is configured and tested for hydrogenation activity in accordance with the procedure of Example III, but in this case the activity tested is for the conversion of the aromatic compound toluene to the cyclic hydrocarbon methylcyclohexane. Activity testing involves the hydrogenation of a number of hydrocarbon mixtures under a range of different reaction conditions, each hydrocarbon mixtures comprising a methylcyclohexane matrix into which a selected fraction of toluene reactant has been blended. The blends are mixed and preheated with a hydrogen gas feed and the gas/liquid mixture is supplied to the catalyst monolith via a steel delivery tube.

As the data in Table 6 suggest, under constant reaction conditions, the extent of toluene conversion decreases with its content in the feed and with increasing $V_L$ (i.e., decreased catalyst-feed stream contact time). Nevertheless, at a $V_L$ of 1.59 cm/s, more than 73% conversion to methylcyclohexane is obtained at all toluene concentration levels tested. Some variations in conversion rate were also observed to result from pressure changes and changes in the H2/oil ratio, and at most concentrations conversions appeared to be maximized at the intermediate rather than the high or low temperatures in the test range. In general, toluene hydrogenation activities are found to be much lower than the 1-octene hydrogenation activities due to the fundamental difference in reaction type, but the ability of the catalyst to achieve high one-pass conversions at appropriate temperatures and flow rates is evident.

A comparison is made between the hydrogenation activity of the structured NiO/alumina catalyst of this Example (honeycomb monolith) and the same catalyst in particle form packed into a trickle bed reactor. For this comparison the NiO/alumina honeycomb of this Example is crushed and sieved to produce 80–200 mesh catalyst particles and the particles are then calcined in an oven at 400° C. at for one hour to remove residual hydrocarbons. A charge of 1.5 cc of the calcined catalyst is then loaded into a tube reactor of 2 cm internal diameter using an SiC powder diluent and SiC end plugs as described in Example I.

The hydrogenation activity of this reactor is tested using a gas/liquid feed wherein the liquid phase comprises 4.2 wt. percent toluene conversion and liquid-hourly-space-velocity (LHSV) of the feed through the reactor.

TABLE 7

Toluene Saturation - Structured 200 cpsi Catalyst

| Bed temp. (° C.) | | $V_L$ | Pressure | $H_2$/Oil | Toluene | Toluene Conversion |
|---|---|---|---|---|---|---|
| Top | Bottom | (cm/s) | (psig) | (NL/L) | conversion (%) | Activity (V/V/sec) |
| 101 | 113 | 5.5 | 220 | 51 | 27.0 | 0.057 |
| 132 | 133 | 5.5 | 220 | 51 | 45.9 | 0.111 |
| 151 | 154 | 5.5 | 220 | 51 | 54.9 | 0.144 |
| 182 | 189 | 5.5 | 220 | 51 | 71.0 | 0.223 |
| 150 | 151 | 5.5 | 220 | 30 | 52.8 | 0.135 |
| 151 | 154 | 5.5 | 220 | 51 | 54.9 | 0.144 |
| 150 | 159 | 5.5 | 220 | 192 | 51.0 | 0.129 |
| 151 | 131 | 1.1 | 220 | 53 | 75.6 | 0.049 |
| 150 | 149 | 2.4 | 220 | 47 | 93.8 | 0.217 |
| 151 | 154 | 5.5 | 220 | 51 | 54.9 | 0.144 |

% toluene in a methylcyclohexane matrix. The test is carried out over a range of temperatures at a liquid hourly space velocity of 95 hour-1, a feed $H_2$/oil ratio of 50 NL/L, and a reactor pressure of 220 psig. The results of this test are then compared with the results obtained using the structured catalyst of this Example under similar reactor operating conditions.

Figure 4:
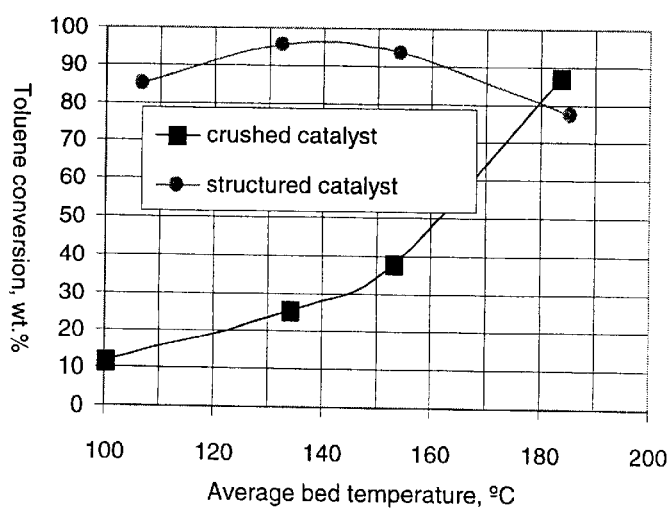
FIG. 4 is a graph comparing the efficiencies of a packed bed reactor and a structured catalyst reactor in accordance with the invention.

The results of this comparison are shown in FIG. 4 of the drawing, which is a plot of conversion efficiency versus reactor operating temperature over a range of operating temperatures. Conversion efficiency is plotted in terms of the percent conversion of toluene to methylcyclohexane in the feed stream. As is evident from a study of FIG. 4, the conversion activity of the structured catalyst significantly exceeds the activity of the crushed catalyst at all reactor temperatures below about 180° C. It is only at temperatures above this point that the activity of the trickle bed reactor becomes competitive.

EXAMPLE VII

Aromatic Saturation—Structured Catalyst with Bulk Catalyst Wall (200 cpsi)

A structured catalyst module, similar to the module of Example VI but incorporating an alumina honeycomb of 200 cpsi cell density, 0.71 mm channel wall thickness and 1 mm channel diameter is prepared for testing. The catalyst preparation procedure of Example IV is followed, and the catalyzed monolith has a catalyst loading of 9.3 wt. % NiO and a BET surface area of 214 $m^2$/g.

This structured catalyst is tested for hydrogenation activity using the testing procedure described in Example III and a toluene-methylcyclohexane liquid feed comprising 4.5 wt. % toluene in a methylcyclohexane matrix. The results generated by that testing are reported in Table 7 below. Included in Table 7 for each of the hydrogenation runs conducted are: the temperatures measured at the top and bottom of the catalyst bed, in ° C., the calculated average linear velocity $V_L$ of liquid reactant flow through the reactor, in cm/sec, the reactor pressure at which the run is carried out, in psig, the H2/oil ratio (liters of hydrogen gas at standard temperature and pressure [NL] to liters of hydrocarbon liquid [L]), the percent conversion of toluene to methylcyclohexane in a single pass through the reactor, and the apparent toluene conversion activity of the catalyst as calculated from the A comparison of the activities demonstrated by the catalyst of this Example VII and the catalyst of Example VI suggests that, depending on reactor operating conditions, improvements in hydrogenation activity by factors ranging from about 2 to about 10 are realized through the use of a catalyst monolith with a higher cell density and smaller channel size.

Of course, the foregoing descriptions and examples are merely illustrative of the invention, and numerous modifications of and variations upon the compositions, processes and apparatus hereinabove described may resorted to by those skilled in the art within the scope of the appended claims.

I claim:

1. A process for carrying out a gas-liquid reaction in the presence of a solid catalyst comprising
   conveying a gas-liquid feed stream through a monolithic structured catalyst bed consisting of a number of reaction channels catalyzed by solid catalysts;
   the liquid in the feed stream being conveyed through the catalyst channels at a superficial liquid linear velocity in the range of 0.01–10 cm/s and
   the gas in the feed stream being conveyed through the catalyst channels in a proportion providing a gas:liquid volume ratio G:L in the range of 1–4000 standard liters of gas/liter of liquid.

2. A process in accordance with claim 1 wherein the gas is hydrogen and the liquid contains at least one hydrocarbon compound selected from the group consisting of unsaturated hydrocarbons and aromatic hydrocarbons.

3. A process in accordance with claim 2 wherein the gas-liquid reaction is a hydrogenation reaction.

4. A process in accordance with claim 3 wherein the superficial liquid linear velocity is in the range of 0.1 to 5.0 cm/s.

5. A process in accordance with claim 4 wherein the gas:liquid ratio is in the range of 10–500 standard liters/liter.

6. A process in accordance with claim 5 wherein the monolithic structured catalyst bed is a honeycomb monolith incorporating a plurality of parallel channels having hydraulic diameters in the range of 0.02–10.0 mm.

7. A process in accordance with claim 6 wherein the hydraulic diameters are in the range of 0.1 to 5.0 mm.

8. A process in accordance with claim 6 wherein the parallel channels are bounded by channel walls having thicknesses in the range of 0.05 to 5.0 mm.

9. A process in accordance with claim 8 wherein the channel walls have a thickness in the range of 0.2 to 2.0 mm.

10. A process in accordance with claim 6 wherein the parallel channels are present in a cell density in the range of 10–3000 channels per square inch (cpsi) of honeycomb cross-section perpendicular to the direction of the channels.

11. A process in accordance with claim 10 wherein the cell density is in the range of 25–400 cpsi.

12. A process in accordance with claim 1 wherein the structured catalyst bed comprises a honeycomb monolith comprising a ceramic honeycomb support and wherein the catalyst is provided as a catalyst dispersion on or within the walls of the honeycomb support.

13. A process in accordance with claim 12 wherein the catalyst dispersion is disposed within a porous coating on the honeycomb monolith.

14. A process in accordance with claim 1 wherein the structured catalyst is a honeycomb monolith composed of catalyst.

15. A process in accordance with claim 1 wherein the gas-liquid reaction is a hydrogenation reaction, the gas contains hydrogen, the liquid includes an aromatic hydrocarbon compound, the reaction is carried out at temperatures in the range of 100–500° C., and the reaction is carried out at pressures in the range of 5–1000 bar.

16. A process in accordance with claim 1 wherein the gas-liquid reaction is a hydrogenation reaction, the gas contains hydrogen, the liquid includes an olefin, the reaction is carried out at temperatures in the range of 20–250° C., and the reaction in carried out at pressures in the range of 5–30 bar.

17. A process for carrying out a three-phase chemical reaction by passing a gas/liquid feed stream through a honeycomb catalyst bed wherein:

the three-phase chemical reaction is a hydrogenation reaction;

the gas contains hydrogen and the liquid includes an aromatic hydrocarbon compound;

the reaction is carried out at temperatures in the range of 100–600° C. and pressures in the range of 5–1000 bar;

the liquid is passed through the catalyst bed at a superficial liquid linear velocity in the range of 0.1 to 5.0 cm/s;

the gas:liquid ratio in the feed stream is in the range of 10–500 standard liters/liter; and the reaction achieves at least 80% hydrogenation of the aromatic hydrogen compound.

18. A process for carrying out a three-phase chemical reaction by passing a gas/liquid feed stream through a honeycomb catalyst bed wherein:

the three-phase chemical reaction is a hydrogenation reaction;

the gas contains hydrogen and the liquid includes an olefin;

the reaction is carried out at temperatures in the range of 20–250° C. and pressures in the range of 5–30 bar;

the liquid is passed through the catalyst bed at a superficial liquid linear velocity in the range of 0.1 to 5.0 cm/s;

the gas:liquid ratio in the feed stream is in the range of 10–500 standard liters/liter; and the reaction achieves at least 80% hydrogenation of the olefin.

19. A process for carrying out a gas-liquid reaction within a chemical reactor containing a solid catalyst comprising:

conveying a gas-liquid feed stream comprising a gas containing hydrogen and a liquid containing an unsaturated or substituted hydrocarbon through a gas-liquid reactor containing a monolithic structured catalyst bed comprising a number of reaction channels catalyzed by solid catalysts;

the liquid in the feed stream being conveyed through the catalyst channels at a superficial liquid linear velocity in the range of 0.01–10 cm/s;

the gas in the feed stream being conveyed through the catalyst channels in a proportion providing a gas:liquid volume ratio G:L in the range of 1–4000 standard liters of gas/liter of liquid; and a conversion rate in excess of 50% of the theoretical conversion limit for the unsaturated or substituted hydrocarbon being obtained in a single pass through the reactor.

20. A process in accordance with claim 19 wherein a conversion rate in excess of 80% of the theoretical conversion limit is obtained in a single pass through the reactor.

* * * * *